US010297349B2

(12) United States Patent
Shin

(10) Patent No.: US 10,297,349 B2
(45) Date of Patent: May 21, 2019

(54) METHOD FOR PROVIDING DISEASE CO-OCCURRENCE PROBABILITY FROM DISEASE NETWORK

(71) Applicant: AJOU UNIVERSITY INDUSTRY-ACADEMIC COOPERATION FOUNDATION, Suwon-si, Gyeonggi-do (KR)

(72) Inventor: Hyun Jung Shin, Seongnam-si (KR)

(73) Assignee: AJOU UNIVERSITY INDUSTRY-ACADEMIC COOPERATION FOUNDATION, Suwon-Si (KR)

( * ) Notice: Subject to any disclaimer, the term of this patent is extended or adjusted under 35 U.S.C. 154(b) by 851 days.

(21) Appl. No.: 14/920,447

(22) Filed: Oct. 22, 2015

(65) Prior Publication Data

US 2016/0350502 A1    Dec. 1, 2016

(30) Foreign Application Priority Data

May 28, 2015  (KR) .................. 10-2015-0074908

(51) Int. Cl.
*G16H 50/20*    (2018.01)
*G06F 19/00*    (2018.01)
*G06N 20/00*    (2019.01)

(52) U.S. Cl.
CPC ............. *G16H 50/20* (2018.01); *G06F 19/00* (2013.01); *G06N 20/00* (2019.01)

(58) Field of Classification Search
CPC ....... G16H 50/20; G06F 19/00; G06F 19/345; G06N 7/005; G06Q 50/22; G06Q 50/24; G06Q 50/26; G06Q 10/04

USPC .......................................................... 706/52
See application file for complete search history.

(56) References Cited

U.S. PATENT DOCUMENTS

| | | | | |
|---|---|---|---|---|
| 2009/0138203 | A1* | 5/2009 | Iossifov | G06F 19/18 702/19 |
| 2013/0116999 | A1* | 5/2013 | Stein | G06F 19/00 703/11 |
| 2013/0151452 | A1* | 6/2013 | Wang | G06F 19/18 706/46 |
| 2014/0207385 | A1* | 7/2014 | Martin | G06F 19/12 702/19 |
| 2014/0214336 | A1* | 7/2014 | Martin | G06F 19/36 702/19 |
| 2015/0220838 | A1* | 8/2015 | Martin | G06F 19/12 706/12 |

(Continued)

OTHER PUBLICATIONS

Davis et al., "Exploring and Exploiting Disease Interactions from Multi-Relational Gene and Phenotype Networks". (Year: 2011).*

(Continued)

*Primary Examiner* — Dave Misir
(74) *Attorney, Agent, or Firm* — Stein IP, LLC

(57) ABSTRACT

Disclosed is a method of providing a disease co-occurrence probability including (a) receiving a disease network in which respective diseases are shown as nodes and a correlation between diseases is shown as an edge between the nodes and (b) calculating, when at least one disease is given, a probability of an occurrence of another disease in addition to the given disease, the corresponding disease which accompanies the given disease, from the disease network.

5 Claims, 8 Drawing Sheets

(56) References Cited

U.S. PATENT DOCUMENTS

2016/0063176 A1* 3/2016 Martin .................. G06F 19/12 703/2

OTHER PUBLICATIONS

Moni et al., "comoR: a software for disease comorbidity risk assessment". (Year: 2014).*

Suthram et al., "Network-Based Elucidation of Human Disease Similarities Reveals Common Functional Modules Enriched for Pluripotent Drug Targets". (Year: 2010).*

Linghu et al., "Genome-wide prioritization of disease genes and identification of disease-disease associations from an integrated human functional linkage network". (Year: 2009).*

Zhang et al., "The expanded human disease network combining protein-protein interaction information". (Year: 2011).*

Lee et al., "The implications of human metabolic network topology for disease comorbidity". (Year: 2008).*

Shin et al., "Graph sharpening plus graph integration: a synergy that improves protein functional classification". (Year: 2007).*

Tsuda et al., "Fast protein classification with multiple networks". (Year: 2005).*

Shin et al., "Protein functional class prediction with a combined graph". (Year: 2009).*

Sun et al., "The integrated disease network". (Year: 2014).*

Kwang-Il Goh et al., The human disease network, May 22, 2007, PNAS vol. 104, No. 21, pp. 8685-8690.

The $8^{th}$ International Conference on Systems Biology, The $4^{th}$ Translation Bioinformatics Conference (ISB/TBC 2014), Oct. 24-27, 2014.

Hyunjung (Helen) Shin, The Translational Disease Network—from Protein Interaction to Disease Co-occurrence, Translational Biomedical Conference/International Conference on Systems Biology (TBC/ISB 2014)\, slides 1-204.

* cited by examiner

METHOD FOR PROVIDING DISEASE CO-OCCURRENCE PROBABILITY FROM DISEASE NETWORK

CROSS-REFERENCE TO RELATED APPLICATION

This application claims the benefit of Korean Patent Application No. 10-2015-0074908, filed on May 28, 2015 in the Korean Intellectual Property Office, the disclosure of which is incorporated herein by reference.

BACKGROUND

1. Field

The present invention relates to a human disease network, and more particularly, to a method of providing a disease co-occurrence probability from a disease network.

2. Description of the Related Art

Recently, a human disease network has developed to provide discernment for building a relationship between genotype and phenotype of human diseases. A disease is generally considered as a result of mutation which causes disorder in fundamental cell function. However, since diseases receive effects by complicated molecular links between a plurality of cell components, it is insufficient to define a disease as a single gene mutation. A series of successful experiments developed in network biology have helped analysis for a human disease network which includes various forms of molecular links such as gene concurrence network, transcriptional control, protein-protein interaction, metabolic pathway, etc.

As initial research on the human disease network, there is a paper [Goh K I, Cusick M E, Valle D, Childs B, Vidal M, Barab'asi A-L: The human disease network Proceedings of the National Academy of Sciences 2007, 104(21): 8685-8690]. Here, it has been tried to find relations between diseases based on genes shared by diseases. According to the paper, most diseases are classified into several clusters. Particularly, in the case of a cancer cluster, cancer cases are tightly connected by a plurality of genes related to cancers in various forms.

So far, understanding of a disease network has developed through growth of theoretical and technical means. However, there is some room for improvement in previous research. The disease network is ready to play a large role on a cell level but have not particularly help medical research or practice yet. General research related to the disease network is still limited to developing a method of forming a network, which seems to be because research related to the disease network has been generally performed by biologists who purely pursue scientific discoveries. However, since results obtained from biologic laboratories are far from helps needed in real situations of providing medical services to patients, such reality does not satisfy doctors/clinics/patients.

SUMMARY

When a patient who is diagnosed with a particular disease is treated, a doctor may want to know whether diseases co-occur by chance or whether the disease increases an occurrence probability of another disease. Accordingly, it becomes more convenient when an answer for a co-occurrence of diseases is given in a numerical form such as a probability value. Currently, general disease networks only provide topology maps among diseases but do not provide such information.

Hereupon, it is an aspect of the present invention to provide a method of providing, when a particular disease is given, a probability of an occurrence of another disease accompanying the particular disease from a disease network.

In accordance with one aspect of the present invention, a method of providing a disease co-occurrence probability includes (a) receiving a disease network in which respective diseases are shown as nodes and a correlation between diseases is shown as an edge between the nodes and (b) calculating, when at least one disease is given, a probability of an occurrence of another disease in addition to the given disease, the corresponding disease which accompanies the given disease, from the disease network.

Operation (b) may include calculating the probability using a correlation degree between the diseases corresponding to the edge.

Operation (b) may include (b1) calculating a score which indicates a degree of the occurrence of the other disease in addition to the given disease, the corresponding disease which accompanies the given disease, using the correlation degree between the diseases corresponding to the edge and (b2) calculating the probability using the calculated score.

Operation (b1) may include (b11) labeling a node corresponding to the given disease as a value of 1 and setting an unlabeled node that is another node in addition to the labeled node as a value of 0 and (b12) calculating the score corresponding to the unlabeled node using the value 1 of the labeled node, the value 0 of the unlabeled node, and the correlation degree corresponding to the edge.

Operation (b12) comprises calculating the score by obtaining f which minimizes H(f) of following Equation, $$\min_f H(f) = (f-y)^T (f-y) + \mu f^T L f$$

wherein f is a vector with a score of each node as a component, y is a vector with a labeled value 1 and a set value 0 of each node as components, µ is a trade-off parameter, and L is a graph Laplacian matrix.

Operation (b2) may include calculating the probability by using following Equation, $$Prob(i)_{|l \in L} = \frac{1}{1 + \exp^{-f_i/\sigma_f}}$$

wherein $Prob(i)_{|l \in L}$ indicates a probability of an occurrence of a disease $l \in L$ corresponding to an ith node, which accompanies a given disease, $f_i$ indicates a calculated score of the ith node, and $\sigma_f$ indicates a scale parameter.

Operation (b2) comprises calculating the probability by using following Equation, $$Prob(i \succ j)_{|l \in L} = \frac{1}{1 + \exp^{-(f_i - f_j)/\sigma_f}}$$

wherein $Prob(i \succ j)_{|l \in L}$ indicates a relative probability of a co-occurrence of ith disease and jth disease, which accompany a given disease $l \in L$, $f_i$ indicates a calculated score of an ith node, $f_j$ indicates a calculated score of a jth node, and $\sigma_f$ indicates a scale parameter.

In accordance with another aspect of the present invention, there is provided a computer-readable recording medium which records a program for executing the method described above.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
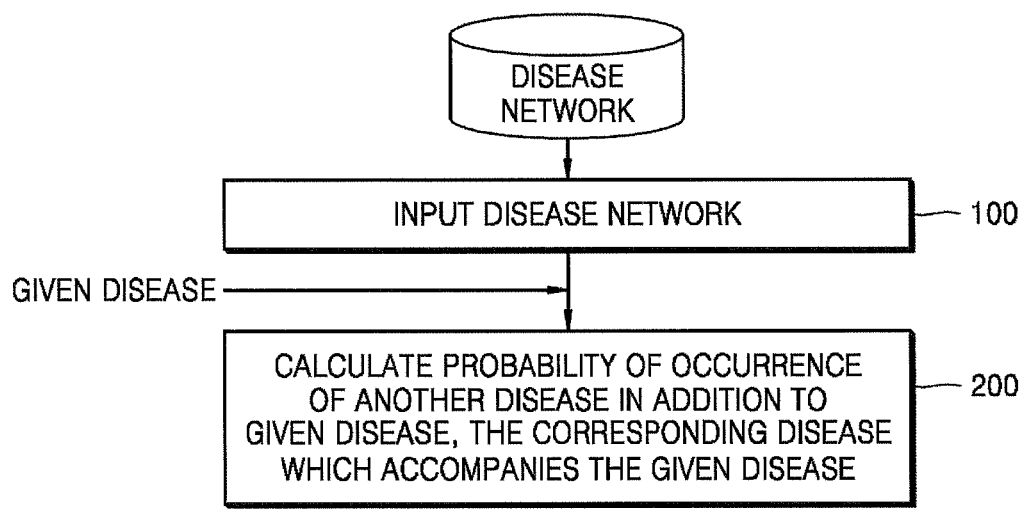
FIG. 1 is a flowchart illustrating a method of providing a disease co-occurrence probability in accordance with one embodiment of the present invention.

Hereinafter, exemplary embodiments of the present invention will be described in detail with reference to the drawings. Hereinafter, throughout the following description and attached drawings, like reference numerals designate like elements and a repetitive description thereof will be omitted. While describing the present invention, when it is determined that a detailed description of well-known functions or components may obscure the points of the present invention, the detailed description will be omitted.

In the embodiment of the present invention, when one or several diseases are given, a degree of an occurrence of another disease accompanying the given diseases will be figured. In the specification, this work will be referred to as "disease scoring". For example, when a person suffers from a particular disease, disease scoring may provide a score or a probability related to in which degree the person is exposed to another disease.

In the embodiment of the present invention, a disease network is used to embody the disease scoring. Also, a graph-based semi-supervised learning (SSL) theory is employed and modified to be appropriate for the disease scoring.

SSL is known as successfully improving classification performance by supporting a classifier using unlabeled data in a field in which some labeled data of which target value to be estimated is known are present and a lot of unlabeled data of which target value to be estimated is unknown are present.

In the case of disease scoring, when a disease from which a person suffers corresponds to labeled data and other diseases in addition thereto correspond to unlabeled data, SSL may become an effective means for the disease scoring.

However, general graph-based SSL has an intention of classification but the disease scoring has an intention of scoring, which is a difference therebetween. For example, in binary classification, a label given to a classifier is a binary value such as +1 or −1 and one class (+1) or another class (−1) is given as an estimation result to unlabeled data. On the other hand, in the scoring, a unary value 1 is given as a label to a scorer and it is necessary to obtain a score for ranking the unlabeled data as an estimation result with respect to the given label.

According to the embodiment of the present invention, there is disclosed a method of providing, when a particular disease is given, a probability of an occurrence of another disease accompanying the particular disease based on the disease scoring described above.

FIG. 1 is a flowchart illustrating the method of providing a disease co-occurrence probability in accordance with one embodiment of the present invention.

Referring to FIG. 1, in S100, a disease network is input.

The disease network is basically formed of nodes and edges, in which respective diseases are shown as nodes and a correlation between diseases is shown as an edge between corresponding diseases.

Figure 2:
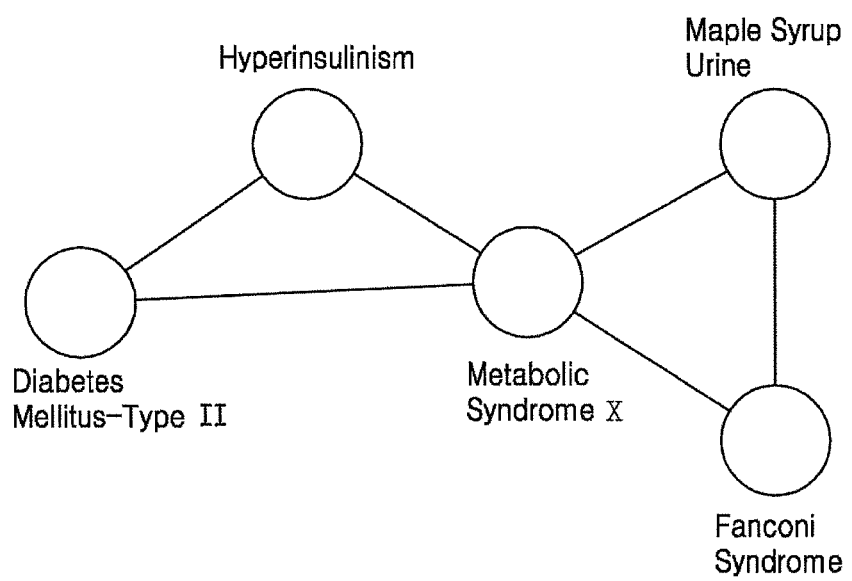
FIG. 2 illustrates a simple example of a disease network.

FIG. 2 illustrates a simple example of the disease network. Referring to FIG. 2, diabetes mellitus-type II, hyperinsulinism, metabolic syndrome X, maple syrup urine, and Fanconi syndrome are shown as nodes and nodes connected by edges indicate that two corresponding diseases have a correlation. For example, since diabetes mellitus-type II and hyperinsulinism are connected by an edge, a correlation is present therebetween.

The disease network may give information on a correlation degree between diseases, for example, 1 is given to a connected case and 0 is given to an unconnected case or basic information for obtaining a correlation degree, for example, a distance between two nodes connected by an edge. For example, the correlation degree between diseases may be obtained by following Equation 1.

$$w_{ij} = \begin{cases} \exp^{-dist(x_i, x_j)/\sigma^2} & \text{if } i \sim j \\ 0 & \text{otherwise} \end{cases} \quad \text{Equation (1)}$$

Here, $x_i$ and $x_j$ indicate nodes, $w_{ij}$ indicates a correlation degree between $x_i$ and $x_j$, dist $(x_i$ and $x_j)$ indicates a distance between two nodes, for example, a Euclidean distance or a cosine distance, $\sigma$ indicates a scale parameter, and i~j indicates that two nodes are connected by an edge.

When one or several particular diseases, for example, diseases from which a patient suffers are given and a correlation degree between corresponding diseases, which corresponds to each edge is obtained from a disease network, in S200, a probability of an occurrence of another disease in addition to the given diseases, which accompanies the given diseases, is calculated using the correlation degree between diseases.

Figure 3:
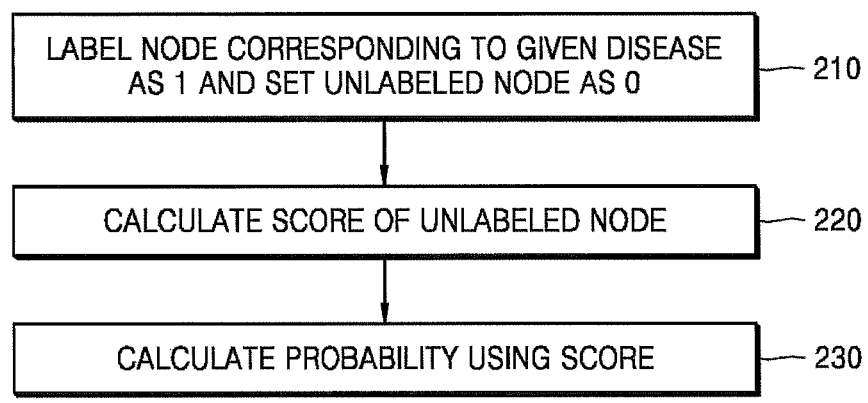
FIG. 3 is a flowchart illustrating S200 in FIG. 1 in more detail.

FIG. 3 is a flowchart illustrating S200 in FIG. 1 in more detail. According to the embodiment of the present invention, in S200, a score which indicates a degree of the occurrence of the other disease in addition to the given diseases, which accompanies the given disease, is calculated using the correlation between the diseases corresponding to the edge in the disease network and then a probability of the occurrence of the corresponding disease accompanying the given diseases is calculated using the calculated score.

Referring to FIG. 3, in S210, nodes corresponding to the given diseases in the disease network are labeled as 1 and unlabeled nodes which are in addition to the labeled nodes are set as 0.

Accordingly, the disease network may be shown as a connected graph G=(V,W) in which V indicates nodes and W indicates edges. A set of the labeled nodes and corresponding label values may be shown as $S_L=\{(x_i,y_i)_{i=1}^{n_l}\}$ and a set of the unlabeled nodes may be shown as $S_U=\{(x_j)_{j=n_l+1}^{n}\}$. Here, from i=1th nodes to $n_l$th nodes are the labeled nodes, from j=$n_l$+1th nodes to nth modes are the unlabeled nodes, and the number of total nodes is n(=$n_l$+$n_u$). $n_l$ number of the labeled nodes are set as unary label $y_i \in \{1\}$, and $n_u$ number of the unlabeled nodes are set as 0 ($y_u$=0).

Then, an object of the disease scoring is to give scores $f_u^T=(f_{n_l+1}, \ldots, f_n)^T$ to the unlabeled nodes $V_U$. Here, $f_{n_l+1}$ indicates a score of a $n_l$+1th node and $f_n$ indicates a score of an nth node.

Figure 4:
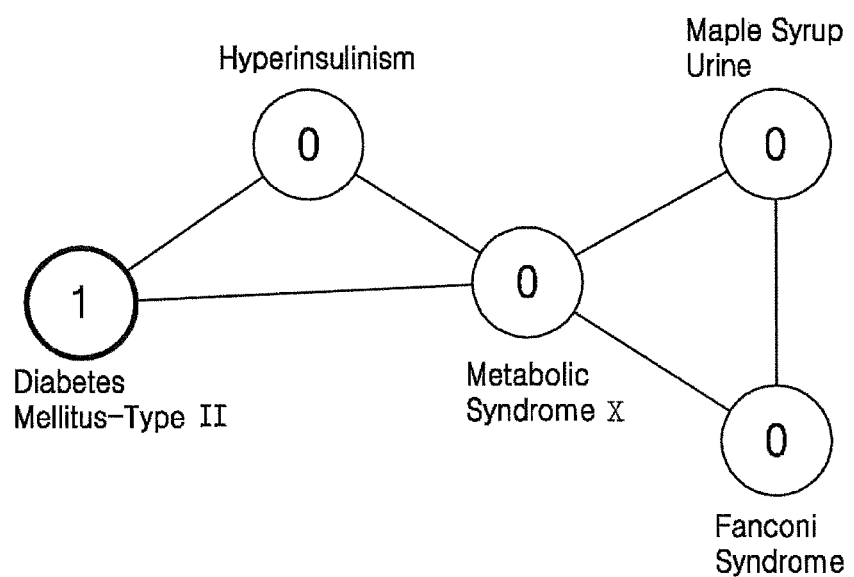
FIG. 4 is a label result of a case in which diabetes mellitus-type II is given as a disease from the disease network of FIG. 2.

FIG. 4 is a label result of a case in which diabetes mellitus-type II is given as a disease from the disease network of FIG. 2. Referring to FIG. 4, a node corresponding to diabetes mellitus-type II is labeled as 1 and other unlabeled nodes are set as 0.

Referring to FIG. 3, in S220, a score corresponding to the unlabeled node, that is, a score which indicates a degree of an occurrence of a disease corresponding to the unlabeled node, which accompanies the given disease, is calculated using a value 1 of the labeled node, a value 0 of the unlabeled node, and a correlation corresponding to an edge.

According to the embodiment of the present invention, to calculate the score described above, when a score of an ith node is $f_i$, it may be assumed that in the case of the labeled node, it is necessary that $f_i$ is close to a given label $y_i$ (loss condition) and is not too different from $f_j$ of an adjacent node (i~j) (smoothness condition). Then, f which minimizes H(f) has only to be obtained according to following Equation 2.

$$\min_f H(f)=(f-y)^T(f-y)+\mu f^T L f \quad \text{Equation (2)}$$

Here, f is a vector with a score of each node as a component, y is a vector with a labeled value (1) and a set value (0) of each node as a component, that is, $y=[y_1, \ldots y_{n_l}, 0, \ldots, 0]^T$. L is a graph Laplacian matrix, and μ is a trade-off parameter of a loss condition corresponding to a first term on a right side and a smoothness condition corresponding to a second term on the right side.

A vector $f_u$ with scores corresponding to the unlabeled nodes from Equation 2 as components may be obtained by following Equation 3.

$$f_u=\mu\{I+\mu(D_{uu}+W_{uu})\}^{-1}W_{ul}y_l \quad \text{Equation (3)}$$

Here, I indicates an identity matrix, $y_l$ indicates a vector with label values 1 of the labeled nodes as components, and a graph Laplacian matrix L, $D_{uu}$, $W_{uu}$, and $W_{ul}$ are defined by following Equations 4 and 5.

$$L=D-W, d_i=\Sigma_j w_{ij}, D=\text{diag}(d_i) \quad \text{Equation (4)}$$

Here, diag ($d_i$) indicates a diagonal matrix and W indicates a correlation degree matrix.

The diagonal matrix D and the correlation degree matrix W are blocked as the labeled nodes and the unlabeled nodes and shown block-wise representation as follows.

$$D=\begin{bmatrix} D_{ll} & 0 \\ 0 & D_{uu} \end{bmatrix}, W=\begin{bmatrix} w_{ll} & w_{lu} \\ w_{ul} & w_{uu} \end{bmatrix} \quad \text{Equation (5)}$$

Here, ll indicates a node labeled from the labeled node, lu indicates a node labeled from the unlabeled node, ul indicates a node unlabeled from the labeled node, and uu indicates a node unlabeled from the unlabeled node.

Figure 5:
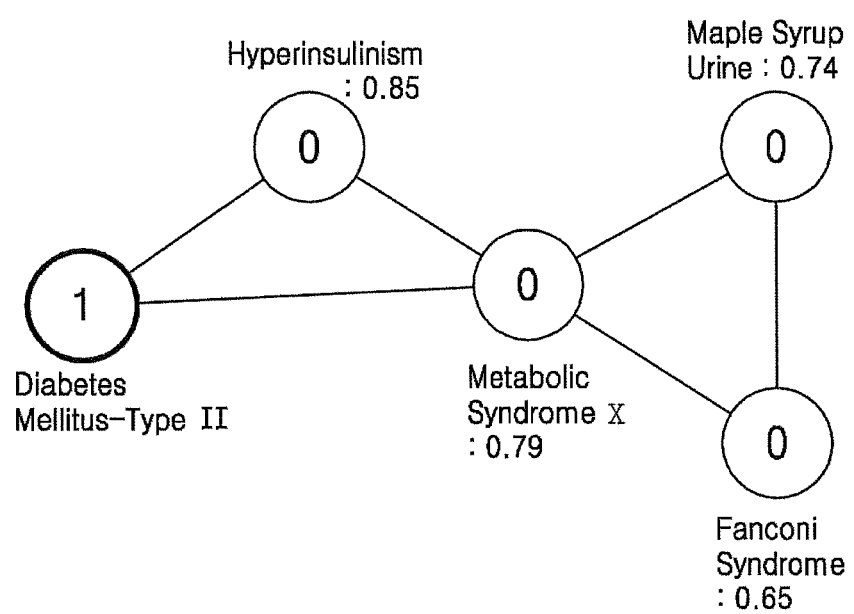
FIG. 5 illustrates an example of a result of calculating scores of nodes unlabeled from the disease network labeled as shown in FIG. 4 in accordance with one embodiment of the present invention.

FIG. 5 illustrates an example of a result of calculating scores of nodes unlabeled from the labeled disease network as shown in FIG. 4 in accordance with one embodiment of the present invention. Referring to FIG. 5, it is shown that scores of hyperinsulinism, metabolic syndrome X, maple syrup urine, and Fanconi syndrome are calculated as 0.85, 0.79, 0.74, and 0.65, respectively.

In S230, a probability of an occurrence of a disease corresponding to each node, which accompanies a given disease, is calculated using a score calculated with respect to each unlabeled node as described above.

The probability may be calculated using following Equation 6.

$$Prob(i)_{|l \in L} = \frac{1}{1+\exp^{-f_i/\sigma_f}} \quad \text{Equation (6)}$$

Here, $Prob(i)_{|l \in L}$ indicates a probability of an occurrence of a disease corresponding to an ith node, which accompanies a given disease $l \in L$, $f_i$ indicates a calculated score of the ith node, and $\sigma_f$ indicates a scale parameter.

In addition, according to the embodiment of the present invention, not only a probability of an occurrence of a certain disease accompanying a given disease but also a relative probability of a co-occurrence of two certain diseases corresponding to unlabeled nodes accompanying the given disease may be obtained.

The relative probability may be calculated using following Equation 7.

$$Prob(i \succ j)_{|l \in L} = \frac{1}{1+\exp^{-(f_i-f_j)/\sigma_f}} \quad \text{Equation (7)}$$

Here, $Prob(i \succ j)_{|l \in L}$ indicates a relative probability of a co-occurrence of ith disease and jth disease, which accompany a given disease $l \in L$, $f_i$ indicates a calculated score of an ith node, $f_j$ indicates a calculated score of a jth node, and $\sigma_f$ indicates a scale parameter. For example, when a value of $Prob(i \succ j)_{|l \in L}$ is greater than 0.5, it means that a probability of an occurrence of an ith disease accompanying a disease $l \in L$ is greater than a probability of an occurrence of a jth disease accompanying the disease $l \in L$.

Figure 6:
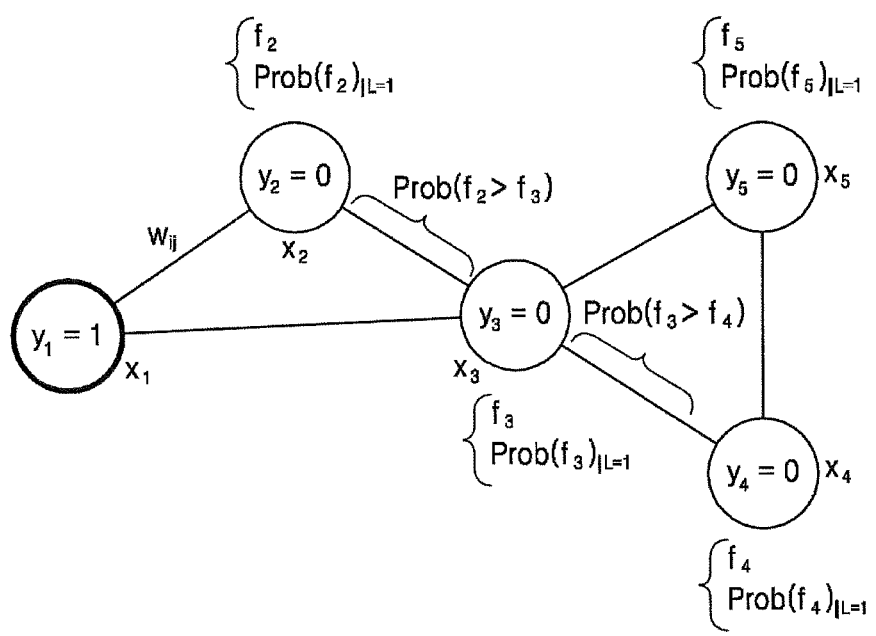
FIG. 6 illustrates general scores and probabilities obtained from the disease network labeled as shown in FIG. 4.

FIG. 6 illustrates general scores and probabilities obtained from the disease network labeled as shown in FIG. 4. As shown in FIG. 6, scores f2, f3, f4, and f5 and probabilities Prob(f2), Prob(f3), Prob(f4), and Prob(f5) may be obtained with respect to unlabeled nodes x2, x3, x4, and x5 and relative probabilities with respect to pairs of the unlabeled nodes may be obtained.

Figure 7:
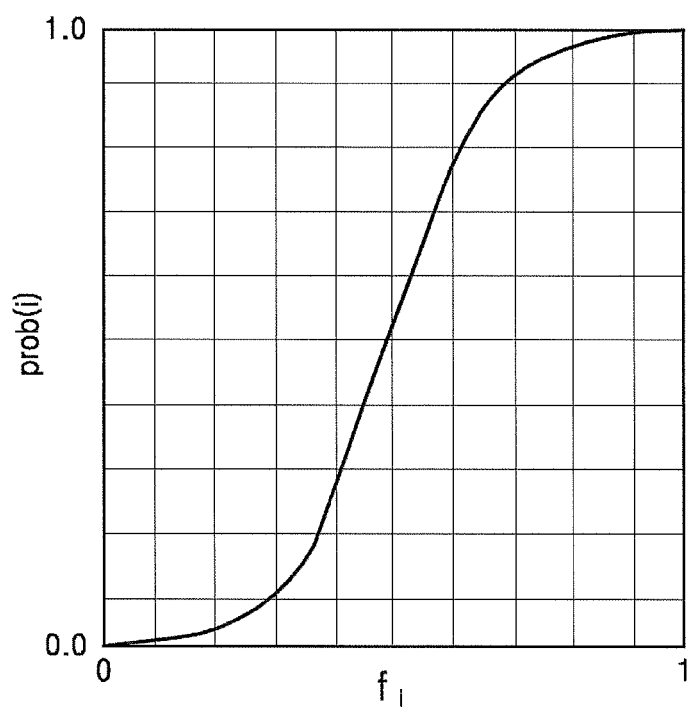
FIG. 7 is a graph of a probability Prob(i) according to a score $f_i$.

FIG. 7 is a graph of a probability Prob(i) according to a score $f_i$. Referring to FIG. 7, a $f_i$ value of 0<$f_i$<1 is obtained with respect to a Prob(i) value of 0<Prob(i)<1.

Figure 8:
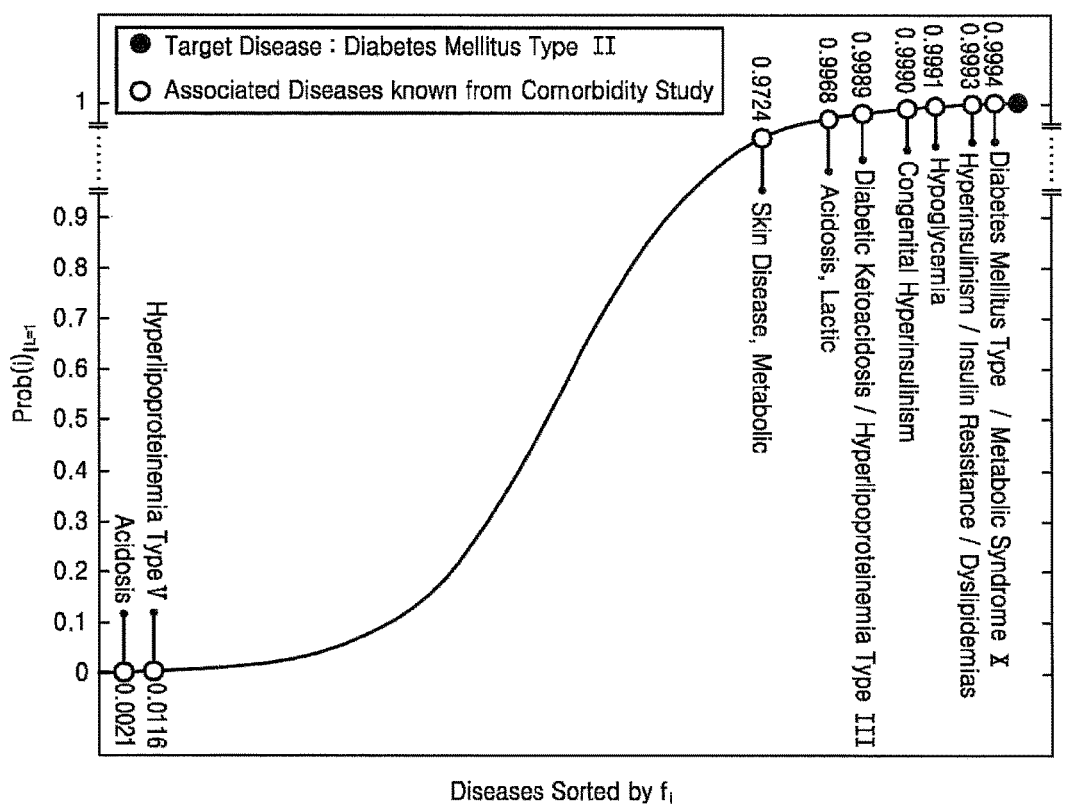
FIG. 8 is a graph illustrating a disease co-occurrence probability calculated in accordance with one embodiment of the present invention.

FIG. 8 is a graph illustrating an example of co-occurrence probabilities of other diseases calculated in accordance with one embodiment of the present invention when diabetes mellitus-type II is given as a disease from which a person suffers. Referring to FIG. 8, it may be checked that several diseases show very high co-occurrence probabilities (>0.97) and several diseases show very low co-occurrence probabilities (>0.02).

In addition, the inventor(s) has(have) verified probability values obtained according to the embodiment of the present invention using a text-mining technology with respect to a document database based on research papers and clinical research data related to diseases which have been published so far. As a result of verification, it was able to check that the probability values obtained in accordance with the embodiment of the present invention correspond to the content of research or investigation related to a co-occurrence of diseases disclosed research papers and clinical research data related to diseases.

Meanwhile, the method according to the embodiment of the present invention described above may be made as a program executable in a computer and may be embodied by using a computer-readable recording medium in a general digital computer which operates the program. The computer-readable recording medium includes a storage medium such as a magnetic storage medium, for example, a read-only memory (ROM), a floppy disc, a hard disc, etc. and an optical reading medium, for example, a compact disc (CD)-ROM, digital versatile disc (DVD), etc.

According to the embodiment of the present invention, when a particular disease is given, a probability of an occurrence of another disease accompanying the particular disease may be provided from a disease network.

As described above, the exemplary embodiments of the present invention have been described. While the present invention has been particularly shown and described with reference to exemplary embodiments thereof, it will be understood by those of ordinary skill in the art that various changes in form and details may be made therein without departing from the spirit and scope of the present invention as defined by the following claims. Therefore the embodiments described above would be considered in a descriptive way, not in a limitative way. The scope of the present invention is shown in the following claims not in the described above, and all differences within a range of equivalents thereof should be understood as included in the present invention.

What is claimed is:

1. A method for medical diagnosis and treatment of a patient based on calculation of a disease co-occurrence probability, comprising:
   (a) receiving a disease network in which each disease is shown as a node and a correlation between two diseases is shown as an edge that connects the two nodes, wherein the two connected nodes represent two corresponding diseases; and
   (b) calculating, when at least one disease is given, a probability of an occurrence of a corresponding disease in addition to the given disease from the disease network,
   wherein operation (b) comprises calculating the probability using a correlation degree between the two corresponding diseases associated with the edge,
   wherein operation (b) comprises:
   (b1) calculating a score which indicates a degree of the occurrence of the corresponding disease in addition to the given disease using the correlation degree between the diseases corresponding to the edge; and
   (b2) calculating the probability using the calculated score, wherein operation (b2) comprises calculating the probability by using following Equation, $$Prob(i)_{|l \in L} = \frac{1}{1 + \exp^{-f_i/\sigma_f}}$$

wherein $Prob(i)_{|l \in L}$ indicates a probability of an occurrence of a disease $l \in L$ corresponding to an ith node, which accompanies the given disease, $f_i$ indicates a calculated score of the ith node, $\sigma_f$ and indicates a scale parameter, and providing for the patient suffering from the given disease the probability of the corresponding disease indicating a degree to which the patient is likely to be exposed or suffering from.

2. The method of claim 1, wherein operation (b1) comprises:
   (b11) labeling a node corresponding to the given disease as a value of 1 and setting an unlabeled node that is another node in addition to the labeled node as a value of 0; and
   (b12) calculating the score corresponding to the unlabeled node using the value 1 of the labeled node, the value 0 of the unlabeled node, and the correlation degree corresponding to the edge.

3. The method of claim 2, wherein operation (b12) comprises calculating the score by obtaining f which minimizes H(f) of following Equation, $$\min_f H(f) = (f-y)^T(f-y) + \mu f^T L f$$

wherein f is a vector with a score of each node as a component, y is a vector with a labeled value 1 and a set value 0 of each node as components, μ is a trade-off parameter, and L is a graph Laplacian matrix.

4. A non-transitory computer-readable recording medium which records a program for executing the method according to claim 1.

5. A method for medical diagnosis and treatment of a patient based on calculation of a disease co-occurrence probability, comprising:
   (a) receiving a disease network in which each disease is shown as a node and a correlation between two diseases is shown as an edge that connects the two nodes, wherein the two connected nodes represent two corresponding diseases; and
   (b) calculating, when at least one disease is given, a probability of an occurrence of a corresponding disease in addition to the given disease from the disease network,
   wherein operation (b) comprises calculating the probability using a correlation degree between the two corresponding diseases associated with the edge,
   wherein operation (b) comprises:
   (b1) calculating a score which indicates a degree of the occurrence of the corresponding disease in addition to the given disease using the correlation degree between the diseases corresponding to the edge; and
   (b2) calculating the probability using the calculated score, wherein operation (b2) comprises calculating the probability by using following Equation, $$Prob(i \succ j)_{|l \in L} = \frac{1}{1 + \exp^{-(f_i - f_j)/\sigma_f}}$$

wherein $Prob(i \succ j)_{|l \in L}$ indicates a relative probability of a co-occurrence of ith disease and jth disease, which accompany the given disease $l \in L$, $f_i$ indicates a calculated score of an ith node, $f_j$ indicates a calculated score of a jth node, and $\sigma_f$ indicates a scale parameter, and providing for the patient suffering from the given disease the probability of the corresponding disease indicating a degree to which the patient is likely to be exposed or suffering from.

* * * * *